US010864241B2

(12) United States Patent
Duttaroy

(10) Patent No.: US 10,864,241 B2
(45) Date of Patent: Dec. 15, 2020

(54) USE OF TOMATO EXTRACT AS ANTIHYPERTENSIVE AGENT AND PROCESS FOR MAKING WATER SOLUBLE SUGAR FREE TOMATO EXTRACT

(71) Applicant: University of Oslo, Oslo (NO)

(72) Inventor: Asim K. Duttaroy, Oslo (NO)

(73) Assignee: Provexis Natural Products Limited, Reading (GB)

(*) Notice: Subject to any disclaimer, the term of this patent is extended or adjusted under 35 U.S.C. 154(b) by 181 days.

(21) Appl. No.: 15/850,107

(22) Filed: Dec. 21, 2017

(65) Prior Publication Data

US 2018/0271926 A1 Sep. 27, 2018

Related U.S. Application Data

(63) Continuation of application No. 14/395,884, filed as application No. PCT/US2013/037524 on Apr. 22, 2013, now abandoned.

(60) Provisional application No. 61/636,813, filed on Apr. 23, 2012.

(51) Int. Cl.
| | | |
|---|---|---|
| *A61K 36/81* | (2006.01) | |
| *A23L 33/105* | (2016.01) | |
| *A61K 9/20* | (2006.01) | |
| *A61K 9/48* | (2006.01) | |
| *A61P 9/12* | (2006.01) | |

(52) U.S. Cl.
CPC ............ *A61K 36/81* (2013.01); *A23L 33/105* (2016.08); *A61K 9/2018* (2013.01); *A61K 9/4858* (2013.01); *A61K 9/4866* (2013.01); *A61K 9/4875* (2013.01); *A61P 9/12* (2018.01); *A23V 2002/00* (2013.01); *A61K 2236/00* (2013.01)

(58) Field of Classification Search
CPC .......... A23V 2002/00; A23V 2200/326; A23V 2250/21; A61K 36/81; A61K 9/4875; A61K 2236/00; A61K 9/2018; A61K 9/4858; A61K 9/4866; A61K 2236/31; A61K 2236/53; A61K 2236/55; A61K 9/00; A61K 9/04; A61K 9/06; A61K 9/10; A23L 33/105; A61P 13/12; A61P 19/06; A61P 25/00; A61P 27/02; A61P 35/00; A61P 3/10; A61P 43/00

See application file for complete search history.

(56) References Cited

U.S. PATENT DOCUMENTS

| | | | |
|---|---|---|---|
| 4,925,690 A | 5/1990 | Odake | |
| 5,502,038 A | 3/1996 | Malinow | |
| 6,436,452 B1 | 8/2002 | Deutz et al. | |
| 6,780,444 B1 | 8/2004 | Reza | |
| 6,958,164 B2 | 10/2005 | Dutta-Roy | |
| 2003/0206983 A1 | 11/2003 | Dutta-Roy | |
| 2004/0191790 A1 | 9/2004 | Tomassen et al. | |
| 2004/0223962 A1 | 11/2004 | Riordan | |
| 2005/0153038 A1 | 6/2005 | Giori | |
| 2006/0035971 A1 | 2/2006 | Youichi et al. | |
| 2006/0078632 A1 | 4/2006 | Woo et al. | |
| 2006/0084614 A1 | 4/2006 | Eckl et al. | |
| 2006/0154877 A1 | 7/2006 | Liu et al. | |
| 2007/0082071 A1 | 4/2007 | Willimann | |
| 2007/0259059 A1 | 11/2007 | Eidenberger | |
| 2008/0009449 A1 | 1/2008 | Prasad | |
| 2009/0053340 A1 | 2/2009 | Crosbie | |
| 2009/0123584 A1 | 5/2009 | O'Kennedy | |
| 2011/0206794 A1 | 8/2011 | O'Kennedy | |
| 2011/0212913 A1 | 9/2011 | O'Kennedy | |
| 2012/0321732 A1 | 12/2012 | O'Kennedy | |
| 2013/0023489 A1 | 1/2013 | Kubow et al. | |
| 2014/0147537 A1 | 5/2014 | O'Kennedy | |
| 2015/0105338 A1 | 4/2015 | O'Kennedy | |
| 2015/0132371 A1 | 5/2015 | Duttaroy | |
| 2016/0375080 A1 | 12/2016 | O'Kennedy | |
| 2019/0175681 A1 | 6/2019 | O'Kennedy | |
| 2020/0054706 A1 | 2/2020 | Mussler et al. | |

FOREIGN PATENT DOCUMENTS

| | | |
|---|---|---|
| CN | 1352941 | 6/2002 |
| CN | 1650951 | 8/2005 |
| DE | 19720767 A1 | 11/1998 |
| EP | 1334728 A2 | 8/2003 |
| EP | 1481669 A1 | 12/2004 |
| EP | 1508325 A1 | 2/2005 |
| EP | 1559421 A1 | 8/2005 |
| EP | 1640001 A1 | 3/2006 |
| EP | 2036568 A1 | 3/2009 |
| FR | 2871378 A1 | 12/2005 |
| JP | 05-201846 A | 8/1993 |
| JP | H09-009892 A | 1/1997 |
| JP | 03-004769 | 1/1999 |
| JP | 2004-137287 | 5/2004 |
| JP | 2004-315386 A | 11/2004 |
| JP | 2006193435 A | 7/2006 |
| JP | 2007-037530 A | 2/2007 |

(Continued)

OTHER PUBLICATIONS

Examination Report of EP 07733050.4, Dated Jan. 13, 2012, 7 Pages.

(Continued)

*Primary Examiner* — Aaron J Kosar

(74) *Attorney, Agent, or Firm* — Linda B. Huber; Nixon Peabody LLP

(57) ABSTRACT

Provided herein is technology relating to tomato extracts and particularly, but not exclusively to preparing and using tomato extracts as an anti-hypertensive agent to modulate blood pressure.

16 Claims, 1 Drawing Sheet

(56) References Cited

FOREIGN PATENT DOCUMENTS

| | | |
|---|---|---|
| JP | 2009240191 A | 10/2009 |
| JP | 2009-538895 A | 11/2009 |
| JP | 2012-36195 A | 2/2012 |
| JP | 2012-506901 A | 3/2012 |
| WO | 94/03421 A2 | 2/1994 |
| WO | WO 99/55350 A1 | 11/1999 |
| WO | WO 00/21507 A2 | 4/2000 |
| WO | WO 2006/085115 A2 | 8/2006 |
| WO | WO 2006/094120 A2 | 9/2006 |
| WO | WO 2007/141495 A1 | 12/2007 |
| WO | WO 2008/080162 A2 | 7/2008 |
| WO | WO 2008/131047 A2 | 10/2008 |
| WO | WO 2010/049707 A2 | 5/2010 |
| WO | WO 2010/049709 A2 | 5/2010 |
| WO | WO 2013/163057 A1 | 10/2013 |
| WO | WO 2014/102546 A1 | 7/2014 |
| WO | 2018083137 A1 | 5/2018 |

OTHER PUBLICATIONS dietandfitnesstoday.com Tomatoes Folic Acid Content, downloaded from the Internet on Oct. 30, 2017, 14 pages.

Franklin, S.J., GRAS Exemption Claim: Claim of Exemption from the Requirement for Premarket Approval Pursuant to Proposed 21 CFR Section 170.36 (c)(1) [62 FR 18938 (Apr. 17, 1997) for Water-Soluable Tomato Concentrate (WSTC), Prepared by Provexis, 2006, 74 pages.

PCT/GB2006/000521 International Search Report and Written Opiniondated Aug. 10, 2006; 9 pages.

PCT/GB2006/000521 International Preliminary Report on Patentability dated Aug. 14, 2007; 7 pages.

PCT/GB2007/002034 International Search Report and Written Opinion dated Oct. 29, 2007; 10 pages.

PCT/GB2007/002034 International Preliminary Report on Patentability dated Dec. 3, 2008; 8 pages.

PCT/GB2009/002593 International Search Report and Written Opinion dated Aug. 10, 2011; 17 pages.

PCT/GB2009/002593 International Preliminary Report on Patentability dated Oct. 11, 2011; 10 pages.

PCT/GB2009/002595 International Search Report and Written Opinion dated Apr. 26, 2010; 25 pages.

PCT/GB2009/002595 International Preliminary Report on Patentability dated May 3, 2011; 18 pages.

PCT/GB2013/053431 International Search Report and Written Opinion dated Feb. 7, 2014; 11 pages.

PCT/GB2013/053431 International Preliminary Report on Patentability dated Jun. 30, 2015; 8 pages.

PCT/US2013/037524 International Search Report and Written Opinion dated Jul. 8, 2013; 11 pages.

PCT/US2013/037524 International Preliminary Report on Patentability dated Oct. 28, 2014; 8 pages.

Chinese Patent Application No. 2007800204350 Examination Report; 12 pages.

GB Application No. 1223365.6 UKIPO Search Report dated Jun. 12, 2013; 2 pages.

Abbey et al. Effect of Quercetin Supplementation on Repeated-Sprint Performance, Xanthine Oxidase Activity, and Inflammation. International Journal of Sport Nutrition and Exercise Metabolism (2011). 91-96.

Abushita et al., Determination of Antioxidant Vitamins in Tomatoes. Food Chemistry (1997), 60(2):207-212.

Amagase et al. Lycium barbarum Attenuates Increased Plasma Stress Hormone Levels Induced by a Short and Intense Exercise Challenge. A Randomized, Double-blind, Placebo-controlled Human Clinical Study. FASEB Journal (2009). 23: 2 pages. Abstract Only.

Anton et al., Thermal inactivation of pectin methylesterase, polygalacturonase, and peroxidase in tomato juice. Journal of Agriculture and Food Chemistry (2002), 50:6153-6159.

Bohm et al., Intestinal absorption of lycopene from different matrices and interactions to other carotenoids, the lipid status, and the antioxidant capacity of human plasma. European Journal of Nutrition (1999), 38(2):1436-6207. Abstract Only.

Burton-Freeman et al. Protective activity of processed tomato products on postprandial oxidation and inflammation: A clinical trial in healthy weight men and women. Mol. Nutr. Food Res. (2012). 56:622-631.

Castell et al. Granule Localization of Glutaminase in Human Neutrophils and the Consequence of Glutamine Utilization for Neutrophil Activity. The Journal of Biological Chemistry (2004). 279(14):13305-13310.

Cermak et al. Nitrate Supplemantation's Improvement of 10-km-Time-Trial Performance in Trained Cyclists. International Journal of Sport Nutrition and Exercise Metabolism (2012). 22:84-91.

Chaouat et al., The Role of Thrombosis in Severe Pulmonary Hypertension, European Respiratory Journal, 1996, vol. 9, pp. 356-363.

De Leeuw et al. Tomato Extract for Hypertension? Cardiovasc Drugs Ther (2009). 23:107-108.

Dutta-Roy et al. Effects of tomato extract on human platelet aggregation in vitro. Platelets (2001), 12(4):218-227.

Friedman et al., Feeding tomatoes to hamsters reduces their plasma low-density lipoprotein cholesterol and triglycerides. Journal of Food Science (2000), 65(5):897-900. Abstract Only.

Hsiao G. et al., Inhibitory effects of lycopene on in vitro platelet activation and in vivo prevention of thrombus formation. Journal of Laboratory and Clinical Medicine (2005), 146(4):216-226.

Hua, J. Diagnosis and Treatment of Deep Venuous Thrombosis Formation in the Lower Limbs (with Analysis of 73 Cases). Zhejiang Medical Journal (1991). 13(6): 3-5.

Hwang et al., Effects of tomato paste extracts on cell proliferation, cell-cycle arrest and apoptosis in LNCaP human prostate cancer cells. BioFactors. 2005, 23:75-84.

Jerjes-Sanchez, C. Venous and arterial thrombosis: a continuous spectrum of the same disease? European Heart Journal. (2005) 26(1):3-4.

Kagome. An Agent used in foodstuffs and beverages for improving fatigue, comprises liquid squeezed from a tomato or component obtained by centrifuging squeezed tomato liquid. Database WPI—Publication No. JP 2006-193435 (Jul. 27, 2006). 1 page. Abstract Only.

Kloek et al. Effect of a Paste from Flavonoid-enriched Tomatoes on Blood Pressure in Spontaneously Hypertensive Rats. FASEB Journal (2004). 18(4-5). Abstract Only.

Lidder et al. Vascular effects of dietary intrate (as found in green leafy vegetables and beetroot) via the nitrate-nitrite-nitric oxide pathway. British Journal of Clinical Pharmacology (2012). 75(3):677-696.

Longo et al. Extract from Harrison's Principals of Internal Medicine. McGraw Hill Companies, Inc. 18th Edition (2012). 9 pages.

Lopez et al., Deep venous thrombosis. American Society of Hematology (2004), 439-456.

Martini et al. Extract from Fundamentals of Anatomy and Physiology. Blood (2009) 8th Edition. Ch. 11. pp. 262-263.

Maruyama et al. Therapeutic strategy targeting coagulation factor Xa in thromboemobolism—Antithrombotic therapy by targeting Xa. Journal of Clinical and Experimental Medicine (2004). 208:393-395.

Miean et al., Flavonoid (myricetin, quercetin, kaempferol, luteolin, and apigenin) content of edible tropical plants. Medicinal & Aromatic Plants Abstracts. 2002, 24(1).

Moco et al. A Liquid Chromatography-Mass Spectrometry-Based Metabolome Database for Tomato. Plant Physiology (2006). 141:1205-1218.

Murphy et al. Whole Beetroot Consumption Actutely Improves Running Performance. J Acad Nutr Diet (2012). 112:548-552.

Naczk et al., Pheolics in cereals, fruits and vegetables: Occurrence, extraction and analysis. Journal of Pharmaceutical and Biomedical Analysis. 2006, 41(5):1523-1542. Abstract.

Nieman et al. Effects of Quercetin and EGCG on Mitochondrial Biogenesis and Immunity. Med Sci Sports Exerc (2009). 41(7):1467-1475.

(56) References Cited

OTHER PUBLICATIONS

O'Kennedy et al., Effects of antiplatelet components of tomato extract on platelet function in vitro and ex vivo: a time-course cannulation study in healthy humans. American Journal of Clinical Nutrition (2006), 84(3):570-579.

O'Kennedy et al., Effects of tomato extract on platelet function: a double-blinded crossover study in healthy humans. American Journal of Clinical Nutrition (2006), 84(3): 561-569.

Oliff, H. Scientific and Clinical Monograph for Pycnogenol. Retrieved from internet: http://abc.herbalgram.org/site/DocServer/Pycnog_FullMono120809_LOW.pdf?docID=1741 on Jan. 1, 2010.

Paran et al. The Effects of Natural Antioxidants from Tomato Extract in Treated but Controlled Hypertensive Patients. Cardiovasc Drugs Ther (2009). 23:145-151.

Roth, GJ. Platelets and blood vessels: the adhesion event. Immunology Today (1992). 13(3):100-105.

Siddesha et al., Inhibition of Angiotensin Converting Enzyme (ACE) by Medicinal Plants Exhibiting Antihypertensive Activity, Recent Progress in Medicinal Plants, 2010, vol. 29, pp. 269-308, Abstract.

Slimestad et al., Journal of Agricultural and Food Chemistry. 2008, 56(7):2436-2441.

Stevenson et al., Comparison of the relative recovery of polyphenolics in two fruit extracts from a model of degradation during digestion and metabolism. Molecular Nutrition & Food Research. 2007, 51(8):939-945.

Talbott et al. Ironman Triathlon Recovery Enhanced By Dietary Supplementation. FASEB Journal (2007). 21(5). 1 page. Abstract Only.

Van Het Hof et al., Carotenoid bioavailability in humans from tomatoes processed in different ways determined from the carotenoid response in the triglyceride-rich lipoprotein fraction of plasma after a single consumption and in plasma after four days of consumption. Journal of Nutrition (2000), 130:1189-1196.

Weber M. et al. Enhance platelet aggregation with TRAP-6 and collagen in platelet aggregometry in patients with venous thromboembolism Thrombosis Research. (2002) 107(6):325-328.

Yamamoto et al., Tomatoes have natural anti-thrombotic effects. British Journal of Nutrition (2003), 90(6): 1031-1038.

Yokoyama et al. New anti-platelet drug and anticoagulation drug—Differences from asprin, warfarin and heparin. Journal of Clinical and Experimental Medicine (2006). Supp vol. (Apoplexy): 17-22.

Zheng et al., Oxygen radicals absorbing capacity of phenolics in blueberries, cranberries, chokeberries, and lingonberries. Journal of Agricultural and Food Chemistry. 2003, 51(2).

Zhu T. et al. Three-Dimensional Reconstruction of Thrombus Formation during Photochemically Induced Arterial and Venous Thrombosis. Annals of Biomedical Engineering Society. (2003) 31(5):515-525.

Zhuang, Q. Blood Coagulation and Fibrinolysis. Chinese Journal of Medicine (1981). 2(11):10-13.

International Search Report and Written Opinion of PCT/EP2017/077993, dated Jan. 23, 2018, 10 Pages.

Lucking et al., Diesel Exhaust Inhalation Increases Thrombus Formation in Man, 2008, European Heart Journal, vol. 29(24), pp. 3043-3051.

USE OF TOMATO EXTRACT AS ANTIHYPERTENSIVE AGENT AND PROCESS FOR MAKING WATER SOLUBLE SUGAR FREE TOMATO EXTRACT

CROSS-REFERENCE TO RELATED APPLICATIONS

This application is a continuation of U.S. patent application Ser. No. 14/395,884 filed Oct. 21, 2014 which is the National Phase of International Application No. PCT/US2013/037524, filed Apr. 22, 2013, which designated the U.S. and that International Application was published under PCT Article 21(2) in English, which claims the benefit of and priority under 35 U.S.C. § 119(e) to U.S. provisional patent application No. 61/636,813 filed Apr. 23, 2012, the entirety of which is hereby incorporated by reference.

FIELD OF INVENTION

Provided herein is technology relating to tomato extracts and particularly, but not exclusively to preparing and using tomato extracts as an anti-hypertensive agent to modulate blood pressure.

BACKGROUND

Cardiovascular disease is a leading cause of morbidity and mortality, and, thus, primary prevention and secondary prevention of cardiovascular disease are public health priorities. High blood pressure, hyperlipidemia, and hyperactivity of platelets are the recognized risk factors for cardiovascular disease. Among these, hypertension is recognized as a major chronic disease. It is defined as a systolic blood pressure above 140 mmHg and/or a diastolic blood pressure above 90 mmHg Hypertension affects up to 30% of the adult population in most countries. However, more than 50% of hypertensive individuals are unaware of their condition. It is estimated that 7.6 million premature deaths (about 13.5% of the global total) and 92 million deaths and disability-adjusted life years (DALYS) (6.0% of the global total) are attributable to high blood pressure. Untreated hypertension can lead to stroke, aneurysm, coronary heart disease (CHD), heart attack, atherosclerosis, ischemic heart disease, left ventricular hypertrophy, encephalopathy, congestive heart failure, hypertensive retinopathy, gout, tachycardia, kidney dysfunction, disability, and death. In addition, hypertension exacerbates the health problems associated with diabetes.

Essential hypertension is not caused by a single identifiable cause but by a cluster of factors, including heredity, age, body weight, environment, and diet. Treatment of moderate to severe hypertension is a life-long commitment and requires drug therapy in combination with changes in lifestyle, including weight reduction if overweight, limitation of alcohol, and reducing salt and fat intake. Essential hypertension can be treated with one of several types of medications, including diuretics, β-adrenoreceptor blockers, inhibitors of angiotensin converting enzyme (ACE), calcium channel blockers, α-adrenoreceptor blockers, vasodilators, and centrally acting agents.

The renin-angiotensin system is a powerful mechanism for controlling blood pressure. When blood pressure falls, the kidneys undergo several intrinsic reactions converting prorenin to renin. When refill enters the bloodstream, it hydrolyzes plasma angiotensinogen to release a peptide called angiotensin I. When aginotensin I circulates to the small vessels of the lungs, it is immediately hydrolyzed to release an 8-amino acid peptide, angiotensin II, by ACE. Angiotensin II circulates in the blood before it is inactivated by angiotensinase. Angiotensin II is a very potent vasoconstrictor and raises blood pressure by severely constricting the arteries, causing an increase in peripheral resistance. It is also able to act on the kidneys to retain both salts and water, leading to an increase in the extracellular fluid volume and thus produces an increase in blood pressure. Finally, angiotensin II causes the adrenal glands to release aldosterone, which in turns increases reabsorption of water and salt in the kidneys.

Thus, one approach to controlling blood pressure is by treatment with ACE inhibitors. ACE inhibitors block the formation of angiotensin II, which normally causes blood vessels to narrow and blood pressure to increase. ACE is not specific for converting angiotensin I to angiotensin II. In addition to its actions on angiotensin, ACE also cleaves a number of other peptides including bradykinin, a nonapeptide. Bradykinin is a potent endothelium-dependent vasodilator, which causes natriuresis and a consequent drop in blood pressure. ACE inhibitors not only decrease the formation of angiotensin II, but also increase the amount of bradykinin, thus further lowering blood pressure.

SUMMARY

In recent years, there has been considerable interest in the potential for using natural food components as functional foods to treat hypertension, especially for patients with borderline to mild high blood pressure that does not warrant the prescription of anti-hypertensive drugs. The mechanism by which some functional foods and nutraceuticals of phenolic type lower blood pressure is mediated by inhibition and down-regulation of expression of ACE and renin. Accordingly, provided herein is technology related to foods and food-derived nutraceuticals that promote cardiovascular health, e.g., by acting as anti-hypertensive agents. In one aspect, the technology relates to potent inhibitors of angiotensin converting enzyme (ACE) activity. The inhibitors are derived from tomatoes and are, e.g., water-soluble, heat stable, and have a molecular mass less than 1000 Da. Modulation of blood pressure by the tomato extract provides a prophylactic and therapeutic benefit in preventing and halting the pathological processes that lead to cardiovascular disease. Accordingly, compositions comprising the tomato extract described are useful in cardiovascular disease prophylaxis, e.g., as an oral tomato extract therapeutic that can be safely and effectively consumed to protect a person's cardiovascular system. In particular, compositions of the sugar-free tomato extracts provided herein are effective as cardio-protective agents especially for people with obesity, insulin resistance, and sedentary life styles.

Accordingly, the technology provided herein is related to a composition comprising a tomato extract (e.g., a water-soluble, sugar-free tomato extract) or an active fraction thereof. In some embodiments, the tomato extract comprises or consists of components that have a molecular mass less than 1000 Da. In some embodiments, the composition is essentially free of lycopene and in some embodiments the composition is essentially free of nucleosides. In some embodiments, the composition is in the form of a dried powder. In some embodiments, the composition is in the form of a solution that will pass through a 0.2 μm filter without loss of solids. According to some embodiments of the technology, the composition is formulated as an oral formulation, e.g., for oral administration. For example, in some embodiments, the composition is formulated in a form selected from the group consisting of a solution, a suspension, a syrup, a tablet, a capsule, a lozenge, a snack bar, a health drink, an insert, and a patch.

Further provided as embodiments of the technology are methods of manufacturing a tomato extract, the method comprising the steps of homogenizing a tomato to produce a tomato homogenate; filtering the tomato homogenate through a filter having a molecular weight cutoff of 1000 Da to produce a filtrate; and collecting the filtrate to provide an extract. In some embodiments, the methods also comprise the steps of freeze-drying the homogenate to produce a freeze-dried homogenate and dissolving the freeze-dried homogenate in water and/or freeze-drying the filtrate to produce a freeze-dried filtrate and dissolving the freeze-dried filtrate in water. In some embodiments, the methods comprise a step of removing a water-soluble sugar from the extract.

Related embodiments provide a composition comprising a tomato extract, obtainable by a method comprising the steps of homogenizing a tomato to produce a tomato homogenate; filtering the tomato homogenate through a filter having a molecular weight cutoff of 1000 Da to produce a filtrate; collecting the filtrate to provide an extract; and removing a water-soluble sugar from the extract.

Embodiments of the technology provided are related to compositions comprising a tomato extract for use as a medicament to treat hypertension and/or for use as a medicament to inhibit angiotensin converting enzyme (ACE) and/or conditions associated with increased ACE activity or levels. In some embodiments, the composition comprising a tomato extract or active fraction thereof is selected from the group consisting of juices, pastes, sauces, and soups. In some embodiments, the compositions are a water-soluble, sugar-free tomato extract. Some embodiments provide a composition for use as a medicament to treat hypertension and/or for use as a medicament to inhibit angiotensin converting enzyme, wherein the tomato extract is made from a cold-break tomato paste. In addition, some embodiments provide a tomato extract for use as a medicament to treat hypertension and/or for use as a medicament to inhibit angiotensin converting enzyme, wherein the composition is produced by a process comprising the steps of diluting in water a cold-break tomato paste of 28-30° Brix and a browning index less than 0.350 AU; removing particulate matter greater than 0.2 µm to produce a solution; and concentrating the solution to form a syrup of 62-65° Brix (see, e.g., International Patent Publications WO/1999/0055350, WO/2007/0141495, and WO/2006/085115, incorporated herein by reference in their entireties for all purposes). Some embodiments provide a tomato extract for use as a medicament to treat hypertension and/or for use as a medicament to inhibit angiotensin converting enzyme, wherein the composition is produced by a process comprising the steps of homogenizing tomatoes; removing particulates by centrifugation and/or ultrafiltration; removing soluble sugars; and eluting non-sugar components in methanol (see, e.g., International Patent Publications WO/1999/0055350, WO/2007/0141495, and WO/2006/085115, incorporated herein by reference in their entireties for all purposes). In some embodiments, the composition is prepared by a method further comprising fractionating components from the non-sugar components using high-pressure liquid chromatography.

In some embodiments, the present invention provides methods of treating a subject comprising: a) identifying a subject having or at risk of having a condition associated with hypertension or ACE activity; and b) administering a composition comprising a tomato extract or active fraction thereof to said subject. In some embodiments, the tomato extract inhibits ACE. In some embodiments, the tomato extract is an aqueous extract. In some embodiments, the tomato is peeled prior to the step of homogenizing. In some embodiments, the tomato extract is in the form of a concentrate or a dehydrate. In some embodiments, the tomato extract is in the form of a concentrate which is at least 2-fold concentrated. In some embodiments, the tomato extract has been dehydrated to give a dry extract. In some embodiments, the dry extract is in the form of a solid or semisolid dosage form. In some embodiments, the extract is contained within a capsule shell. In some embodiments, the extract contains a substantially heat stable water soluble compound or compounds having a molecular weight of less than 1000. In some embodiments, the condition or disorder is selected from the group consisting of stroke, aneurysm, coronary heart disease (CHD), heart attack, atherosclerosis, ischemic heart disease, left ventricular hypertrophy, encephalopathy, congestive heart failure, hypertensive retinopathy, gout, tachycardia, kidney dysfunction, diabetes, and disease states associated with ACE activity and/or hypertension. In some embodiments, the extract is in the form of an active fraction of the fruit capable of passing through an ultrafiltration filter having a molecular weight cut-off of 1000 and containing a substantially heat stable, colorless or straw-colored, water soluble compound or compounds having a molecular weight of less than 1000. In some embodiments, the composition comprising a tomato extract or active fraction thereof is selected from the group consisting of juices, pastes, sauces, and soups.

In some embodiments, the present invention provides methods for the treatment a condition associated with hypertension, the method comprising administering to a patient in need of such treatment a therapeutically effective amount of a fruit extract having anti-hypertension activity, and wherein the fruit extract is obtained from a fruit of the plant family Solanaceae by a process comprising the steps of homogenizing the flesh of the fruit to form a homogenate and removing solids therefrom.

In another related aspect of the technology, embodiments of the technology provide a pharmaceutical formulation comprising a tomato extract and an excipient suitable for treating hypertension or for inhibiting ACE. In addition, embodiments provide an anti-hypertension agent and/or an ACE inhibitor comprising a tomato extract. Embodiments of the technology are also provided relating to a method of treating a subject comprising identifying a subject having or at risk of having hypertension; and administering a composition comprising a tomato extract or active fraction thereof to said subject. Additional embodiments will be apparent to persons skilled in the relevant art based on the teachings contained herein.

DESCRIPTION OF THE FIGURES

FIG. 1 provides a graph depicting the effect of sugar free tomato extract on inhibition of activity of pure ACE protein.

DETAILED DESCRIPTION

Provided herein is technology related to compositions and uses related to anti-hypertensive agents in tomatoes. In particular, during the development of embodiments of the technology, it was discovered that sugar free tomato extracts prepared as described herein exhibit an ability to reduce ACE activity.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

It will be appreciated that there is an implied "about" prior to the temperatures, concentrations, times, etc. discussed in the present teachings, such that slight and insubstantial deviations are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present teachings.

Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., *Molecular Cloning: A Laboratory Manual* (Third ed., Cold Spring Harbor Laboratory Press, Cold Spring Harbor, N.Y. 2000). The nomenclatures utilized in connection with, and the laboratory procedures and techniques described herein are those well known and commonly used in the art.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the term "water soluble" as applied to a tomato extract refers to the tomato extract being soluble at room temperature, e.g., at approximately 25° C. However, this definition is not limiting as some compositions comprising extracts according to the technology are soluble at lower temperatures, e.g., at temperatures as low as approximately 4° C.

As used herein, the term "active" as applied to a composition, extract, substance, mixture, solid, liquid, etc., refers to having the ability to modulate (e.g., lower) blood pressure and/or modulate (e.g., inhibit) ACE activity.

A "subject" is an animal, such as a vertebrate, and preferably a mammal, such as a human. Mammals are understood to include, but are not limited to, murines, simians, humans, bovines, ceroids, equines, porcines, canines, felines, etc.

An "effective amount" is an amount sufficient to effect beneficial or desired results. An effective amount can be administered in one or more administrations.

As used herein, the term "effective amount" refers to the amount of a composition sufficient to effect beneficial or desired results. An effective amount can be administered in one or more administrations, applications, or dosages and is not intended to be limited to a particular formulation or administration route.

As used herein, the term "co-administration" refers to the administration of at least two agents or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent.

As used herein, the term "pharmaceutical composition" refers to the combination of an active agent with a carrier, inert or active, making the composition especially suitable for therapeutic use.

The terms "pharmaceutically acceptable" or "pharmacologically acceptable", as used herein, refer to compositions that do not substantially produce adverse reactions, e.g., toxic, allergic, or immunological reactions, when administered to a subject. Pharmaceutically acceptable compositions are known in the art such as those described in, for example, *Remingtons Pharmaceutical Sciences*, Mack Publishing Co. (A. R. Gennaro edit. 1985), explicitly incorporated herein by reference for all purposes.

As used herein, the term "treating" includes reducing or alleviating at least one adverse effect or symptom of a disease or disorder through introducing in any way a therapeutic composition of the present technology into or onto the body of a subject. "Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

As used herein, "therapeutically effective dose" refers to an amount of a therapeutic agent sufficient to bring about a beneficial or desired clinical effect. Said dose can be administered in one or more administrations. However, the precise determination of what would be considered an effective dose may be based on factors individual to each patient, including, but not limited to, the patient's age, size, type or extent of disease, stage of the disease, route of administration, the type or extent of supplemental therapy used, ongoing disease process, and type of treatment desired (e.g., aggressive versus conventional treatment).

Embodiments of the Technology

Although the disclosure herein refers to certain illustrated embodiments, it is to be understood that these embodiments are presented by way of example and not by way of limitation.

Tomato Extracts

Provided herein are tomato extracts having activities that are beneficial for cardiovascular health. For example, data collected during the development of particular embodiments of the technology described show that the extract decreased ACE activity in normal serum in a dose dependent manner. In addition, data collected also demonstrate that the active compounds in the tomato extract are water-soluble and have a very different structure that the lipid-soluble compounds. The extract can be fractionated to isolate one or more active fractions therein by, for example, molecular weight filtration or chromatography on a suitable support. In some embodiments, the fractionation, e.g., using a Lipidex-1000 column, results in the removal of lipids. In some embodiments, the extract is fractionated by solid phase extraction. During the development of the technology provided, experiments carried out on tomato extract revealed that the active components of the extract pass through an ultrafiltration membrane having molecular weight cut-off 1000 Da. In addition, the active extract is colourless, water soluble, and does not lose activity when boiled. In some embodiments, the active compound in the extract is not lycopene.

The technology encompasses extracts from tomato as well as other members of the family Solanaceae. Solanaceae is a family of flowering plants including, e.g., *Datura, Mandragora* (mandrake), *Atropa belladonna* (deadly nightshade), *Lycium barbarum* (wolfberry), *Physalis philadelphica* (tomatillo), *Physalis peruviana* (Cape gooseberry flower), *Capsicum* (chili pepper, bell pepper), *Solanum* (potato, tomato, eggplant), *Nicotiana* (tobacco), and *Petunia*. In some embodiments, the technology comprises extracts from the genus *Solanum*, for example, tomato (e.g., *S. lycopersicum*); potato (e.g., *S. tuberosum*); eggplant (e.g., *S. melongena*); Giant Devil's fig (e.g., *S. chrysotrichum*); Ethiopian eggplant and gilo (e.g., *S. aethiopicum*); naranjilla or lulo (e.g., *S. quitoense*); Turkey berry (e.g., *S. torvum*); pepino (e.g., *S. muricatum*); "bush tomatoes" of Australia; and other members of the formerly independent genera *Lycopersicon* (the tomatoes) and *Cyphomandra*.

The technology encompasses compositions comprising embodiments of the extracts produced as described in the Examples and as described, e.g., in International Patent Publications WO/1999/0055350, WO/2007/0141495; and WO/2006/085115 incorporated herein by reference in their entireties for all purposes. It addition, the technology encompasses compositions, methods of producing compositions, pharmaceutical formulations, and other technology disclosed, e.g., in U.S. Pat. No. 6,958,164; EP 1334728; AU 772923; and DK 1083912, incorporated herein by reference in their entireties for all purposes. The technology encompasses modifications of the compositions, methods, and technologies provided in these publications that are obvious to one of skill in the art.

For example, due to the presence in tomatoes of the anti-ACE and/or anti-hypertensive agents, some embodiments of the technology comprises the use of whole, chopped, pureed, sliced, or other non-fractionated forms of tomatoes (juices, pastes, sauces, soups, garnishes, etc.) to reduce blood pressure or inhibit ACE. In preferred embodiments, these various forms comprise an active fraction that reduces blood pressure and/or inhibits ACE activity in a target population (i.e., persons in need of blood pressure reduction or in need of treatment of diseases associated with increased ACE activity). Thus, while whole tomatoes or tomatoes that have been chopped or otherwise comminuted but not fractionated may be used for the purposes of the invention, in some embodiments, a tomato extract for reducing blood pressure and/or inhibiting ACE activity is an aqueous extract of tomato. Such extracts may be prepared by homogenizing the flesh of a tomato, with or without its skin, and then filtering the homogenate to remove solids. Preferably, substantially all water-insoluble solids are removed, for example, by centrifugation and/or filtration.

In each case, removal of the solids has the effect of removing fragments of skin containing lycopene. Thus, in some embodiments, the tomato extracts encompassed by the technology are water soluble extracts that are substantially free of lycopene. The aqueous filtrate may be subjected to further fractionation to provide an active fraction containing a compound or compounds responsible for the biological or therapeutic effects described herein. Alternatively, the filtrate may be evaporated to give a dry water-soluble extract. Filtration of the tomato homogenate may be accomplished in a single stage, or in a series of filtration steps, starting with a relatively coarse filtration or centrifugation step to remove larger particles of tomato skin and/or other water-insoluble fragments of tomato flesh. Some embodiments provide that the tomatoes are peeled as a first step to remove a large portion of the tomato skin prior to homogenization. Further filtration steps may then be used to produce a substantially clear solution, e.g., a solution that will pass through a 0.2 µm filter without loss of solids.

Thus, in embodiments of the technology, the tomato extract is a water soluble extract substantially free of lycopene and capable of passing through a 0.2 µm filter without loss of solids. Moreover, in some embodiments, native sugars are removed from the tomato extracts. An advantage of removing the sugars is that the activity of the extracts is concentrated and the extracts tend to be less sticky and easier to process in the solid form.

Alternatively, commercially available tomato pastes may be used as the starting material for the preparation of the extracts. The tomato pastes are typically diluted with water and then water-insoluble solids are removed, e.g., by centrifugation and/or filtration to give a substantially clear solution. Where the starting material for the preparation of the extracts is a tomato paste, it is preferably one that has been produced by means of a "cold-break" process rather than a "hot-break" process. The terms "cold-break" and "hot-break" are well-known in the field of tomato processing and commercially available tomato pastes are typically sold as either hot-break or cold-break pastes. Cold-break pastes can be prepared by a process involving homogenization of the tomato followed by a thermal processing step in which the tomatoes are heated to temperature of no more than about 60° C., in contrast to hot-break pastes where the homogenized tomatoes are subjected to thermal processing at temperatures of about 95° C. (see, for example, Anthon et al., *J. Agric. Food Chem.* 2002, 50: 6153-6159).

In some embodiments, an aqueous extract of tomatoes or tomato paste is produced by enzyme digestion of pectins and starch in homogenised fruit or paste, followed by removal of suspended solids from the homogenate, and micro- or ultra-filtration to remove large molecular weight proteins and remaining polysaccharides. The extract can be refined by removing simple sugars, for example, glucose, fructose, and sucrose, leaving a concentrated water-soluble extract that contains a wide variety of low molecular weight (<1000 Da) non-sugar tomato components. Removal of simple sugars can be carried out by crystallization, for example, using low-temperature ultrasound-assisted crystallization or ethanol precipitation of crystalline glucose and fructose. Alternatively, simple sugars can be separated from other extract components by a chromatographic procedure, for example, selective adsorption of bioactive extract components from the aqueous solution onto a polystyrene-based resin material, thus allowing the selective removal of glucose, fructose, and sucrose in the waste stream. The adsorbed non-sugar compounds are then recovered from the adsorbent resin material by elution with ethanol followed by removal of the ethanol by evaporation. The non-sugar components can be dried into a water-soluble powder by spray drying or drum drying or optionally resuspended in water to give an aqueous syrup. Aqueous extracts prepared are provided by embodiments of the technology. For example, in some embodiments the extracts are dried powders, a concentrate, a dehydrate, a semi-solid, etc. Concentrates are, in some embodiments, at least 2-fold concentrated, at least 4-fold concentrated, at least 8-fold, at least 40-fold, at least 100-fold, at least 200-fold, or at least 1000-fold concentrated.

Sugar-free tomato extracts, for example, extracts as described herein, typically contain a variety of compounds of molecular weight<1000 Da and are provided herein as embodiments for use according to the technology described. Additionally, the tomato extracts are effective if they have no or low nucleoside content. Accordingly, in some embodiments, the tomato extract that find use in accordance with the technology have no or less that 10 nM nucleosides contained therein.

The tomato extracts encompassed by the technology comprise a number of bioactive components, e.g., phenolic compounds, amino acids, amino acid conjugates, and tomato flavor compounds. In some embodiments, the extracts comprise phenolic compounds selected from flavonoids and flavonoid derivatives, for example, derivatives of quercetin, kaempferol, and naringenin; hydroxycinnamic acids and derivatives, for example, ferulic acid, coumaric acid, and their conjugates; benzoic acids and derivatives such as benzoic acid, hydroxybenzoic acid, gallic acid, salicylic acid, and conjugates. In some embodiments, the extract comprises amino acids selected from tyrosine and hydroxytyrosine, phenylalanine, glutamine, and their conjugates. In some embodiments, the extracts comprise a flavor compound such as a hexanal derivative, dimethylsulfide, beta-damascenone, 3-methylbutyric acid, eugenol, and/or methional.

In some embodiments, the tomato extracts is sub-fractionated by HPLC to produce three subfractions on the basis of polarity.

Pharmaceutical and Nutraceutical Formulations

The extracts or active fractions thereof may be formulated for oral administration. As such, they can be formulated as, e.g., solutions, suspensions, syrups, tablets, capsules, lozenges, snack bars, inserts, and patches. Such formulations are prepared in accordance with methods well known in the art. For example, in some embodiments the extracts or active fractions are formed into syrups or other solutions for administration orally. As an exemplary embodiment of an orally administrable composition, the technology contemplates, e.g., health drinks, optionally comprising one or more excipients selected from sugars, vitamins, flavouring agents, colouring agents, preservatives, and thickeners. In some embodiments, tonicity adjusting agents such as sodium chloride or a sugar are added to provide a solution of a particular osmotic strength, for example an isotonic solution. One or more pH-adjusting agents, such as buffering agents, are also used in some embodiments to adjust the pH to a particular value and, e.g., maintain it at that value. Examples of buffering agents include sodium citrate/citric acid buffers and phosphate buffers.

In some embodiments, the extracts or active fractions thereof are dried, e.g., by spray drying or freeze drying, and the dried product formulated in a solid or semi solid dosage form, for example, as a tablet, lozenge, capsule, powder, granulate, or gel. For example, simple dried extracts are prepared according to particular embodiments of the technology without any additional components. Alternatively, some embodiments provide dried extracts that are prepared by adsorption onto a solid support, for example, a sugar such as sucrose, lactose, glucose, fructose, mannose; a sugar alcohol such as xylitol, sorbitol, or mannitol; or a cellulose derivative. Other particularly useful adsorbents include starch-based adsorbents such as cereal flours, for example, wheat flour and corn flour.

For tablet formation, the dried extract is typically mixed with a diluent such as a sugar, e.g., sucrose or lactose; sugar alcohols such as xylitol, sorbitol, and mannitol; or modified cellulose or cellulose derivative such as powdered cellulose, microcrystalline cellulose, or carboxymethyl cellulose. Tablets will also typically contain one or more excipients selected from granulating agents, binders, lubricants, and disintegrating agents. Examples of disintegrants include starch and starch derivatives, and other swellable polymers, for example, crosslinked polymeric disintegrants such as cross-linked carboxymethylcellulose, crosslinked polyvinylpyrrolidone, and starch glycolates. Examples of lubricants include stearates such as magnesium stearate and stearic acid. Examples of binders and granulating agents include polyvinylpyrrolidone. Where the diluent is not naturally very sweet, a sweetener can be added, for example, ammonium glycyrrhizinate or an artificial sweetener such as aspartame or sodium saccharinate.

In some embodiments, dried extracts are formulated as powders, granules, or semisolids for incorporation into capsules. For example, in relation to embodiments in the forms of powders, the extracts are formulated together with any one or more of the excipients defined above in relation to tablets, or can be presented in an undiluted form. For example, in relation to embodiments in the forms of a semisolid, the dried extracts are dissolved or suspended in a viscous liquid or semisolid vehicle such as a polyethylene glycol, or a liquid carrier such as a glycol, e.g., propylene glycol, glycerol, or a vegetable or fish oil such as an oil selected from olive oil, sunflower oil, safflower oil, evening primrose oil, soya oil, cod liver oil, herring oil, etc. Such extracts can be filled into capsules of either the hard gelatine or soft gelatine type or made from hard or soft gelatine equivalents.

In some embodiments, dried extracts are provided in a powder form for incorporation into snack food bars such as fruit bars, nut bars, and cereal bars. For example, in relation to embodiments in the form of a snack food bar, the dried extracts are admixed with any one or more ingredients selected from dried fruits such as sun-dried tomatoes, raisins and sultanas; or groundnuts or cereals such as oats and wheat.

In some embodiments, dried extracts are provided in a powder form for reconstitution as a solution. As such they can also contain soluble excipients such as sugars, buffering agents such as citrate and phosphate buffers, and effervescent agents formed from carbonates, e.g., bicarbonates such as sodium or ammonium bicarbonate, and a solid acid, for example, citric acid or an acid citrate salt. In some embodiments, dried extract is provided in powder form optionally together with a preferred solid (e.g. powdered) excipient for incorporation into capsules, for example, a hard gelatine capsule. In some embodiments, the dried extract is one from which substantially all native sugars have been removed. In exemplary embodiments, a solid or semisolid dosage form related to the technology contains up to about 1000 mg of the dried extract, for example, up to about 800 mg. The extracts are presented in some embodiments as food supplements or food additives, or can be incorporated into foods, for example functional foods or nutraceuticals.

In some embodiments of the technology, the compositions are provided in the form of unit dosage forms containing a defined concentration of extract or active fraction thereof. Such unit dosage forms can be selected so as to achieve a desired level of biological activity. For example, a unit dosage form can contain an amount of up to 1000 mg (dry weight) of an extract or active fraction, more typically up to 800 mg, for example 50 mg to 800 mg, e.g., 100 mg to 500 mg. Particular amounts of extract or active fraction that may be included in a unit dosage form may be selected from 50 mg, 100 mg, 150 mg, 200 mg, 250 mg, 300 mg, 350 mg, 400 mg, 450 mg, 550 mg, 600 mg, 650 mg, 700 mg, 750 mg, and 800 mg. In addition, the compositions can be included in a container, pack, or dispenser together with instructions for administration.

Pharmaceutical and Nutraceutical Uses

For use according to the technology disclosed, e.g., as an anti-hypertensive agent and/or an ACE inhibitor, the quantity of extract or active fraction administered to a patient per day will depend upon the strength of the extract and the particular condition or disease under treatment and its severity, and ultimately it will be at the discretion of the physician. The amount administered however will typically be a non-toxic amount effective to bring about the desired result.

For example, a typical daily dosage regime for a human patient potentially at risk of suffering from high blood pressure may be from 0.0001 to 0.1 gram, e.g., in the range of 0.001 to 0.05 gram per kilogram body weight. When an active fraction is isolated and administered, the amount of solid material administered can be reduced by an amount consistent with the increased purity of the fraction. Typically, at least 100 mg (dry weight or dry weight equivalent), at least 200 mg, and usually at least 500 mg of the extract will be administered per day to a human patient. In some embodiments comprising administration of the compositions, the compositions are administered in single or multiple dosage units per day, for example, from one to four times daily, or from one or two times daily. Moreover, embodiments provide that the extracts of the invention are administered in solid, liquid, or semi-solid form. For example, the extracts are administered according to some embodiments in the form of tomato juice or concentrates thereof alone or in admixture with other fruit juices such as orange juice.

In some embodiments, provided herein are methods of treatment comprising: administering a pharmaceutically effective amount of a tomato extract, a fraction or derivative thereof, or a pharmaceutical preparation thereof, alone or in combination with another agent, to a subject with a condition associated with hypertension. In some embodiments, the administration causes a reduction in blood pressure or an inhibition of ACE. In some embodiments, the administration causes elimination of one or more symptoms of high blood pressure or ACE activity, prevention of increased severity of one or more symptoms of the condition, and/or reduction, prevention, or elimination of further diseases or conditions.

In some embodiments, a subject is tested to assess the presence, the absence, or the level of a disease (e.g., hypertension or condition related to hypertension and/or ACE activity), e.g., by assaying or measuring a biomarker, a metabolite, a physical symptom, an indication, etc., to determine the risk of or the presence of hypertension and/or a related disorder, and thereafter the subject is treated with a composition comprising a tomato extract, an active fraction thereof, or a pharmaceutical formulation thereof, alone or in combination with other agents based on the outcome of the test. In some embodiments, a patient is tested, treated, and then tested again to monitor the response to therapy. In some embodiments, cycles of testing and treatment may occur without limitation to the pattern of testing and treating (e.g., test/treat, test/treat/test, test/treat/test/treat, test/treat/test/treat/test, test/treat/treat/test/treat/treat, etc), the periodicity, or the duration of the interval between each testing and treatment phase.

For example, in some embodiments, the methods provided comprise testing a subject for a disease or condition related to hypertension or ACE activity, followed by administering a composition comprising a tomato extract, an active fraction thereof, or a pharmaceutical formulation thereof, alone or in combination with other agents. In some embodiments, the methods comprise administering to a subject a composition comprising a tomato extract, an active fraction thereof, or a pharmaceutical formulation thereof, alone or in combination with other agents, followed by testing the subject for a disease or condition related to hypertension or ACE activity. In some embodiments, the methods provided comprise testing a subject for a disease or condition related to hypertension or ACE activity, followed by administering a composition comprising a tomato extract, an active fraction thereof, or a pharmaceutical formulation thereof, alone or in combination with other agents, followed by a second round of testing for a disease or condition related to hypertension or ACE activity (e.g., to monitor the effect of the treatment). In some embodiments, methods comprise testing a subject for a disease or condition related to hypertension or ACE activity, followed by administering a composition comprising a tomato extract, an active fraction thereof, or a pharmaceutical formulation thereof, alone or in combination with other agents, followed by a second round of testing for a disease or condition related to hypertension or ACE activity, and a second administration of a composition comprising a tomato extract, an active fraction thereof, or a pharmaceutical formulation thereof, alone or in combination with other agents, with this second administration being modified in dose, duration, frequency, or administration route in a manner dependent upon the results of the prior testing.

In some embodiments, a composition comprising a tomato extract, an active fraction thereof, or a pharmaceutical formulation thereof, is co-administered with one or more additional therapeutic agents or medical interventions. In some embodiments, co-administration involves co-formulation of two or more agents together into the same medicament. In other embodiments, the agents are in separate formulations but are administered together, either simultaneously or in sequence (e.g., separated by one or more minutes, hours, days, etc.). In some embodiments, where a synergistic or additive benefit is achieved, the co-administered agent may be provided at a lower dose than would normally be administered if that agent were being used in isolation to treat the disease or condition. For example, in some embodiments, one or more of the following agents or interventions is co-administered or co-applied with a composition comprising a tomato extract, an active fraction thereof, or a pharmaceutical formulation thereof: low-fat diet, low-salt diet, exercise, a relaxation technique (e.g., meditation, biofeedback), an ACE inhibitor, smoking cessation, high-fruit diet, weight loss, reduced alcohol consumption, reduced caffeine consumption, vitamin D, and/or other changes in diet such as changing the diet to a diet rich in nuts, whole grains, fish, poultry, fruits, and vegetables.

In some embodiments, a single dose of a composition comprising a tomato extract, an active fraction thereof, or a pharmaceutical formulation thereof is administered to a subject. In other embodiments, multiple doses are administered over two or more time points, separated by hours, days, weeks, etc. In some embodiments, compositions are administered over a long period of time (e.g., chronically), for example, for a period of months or years (e.g., 1, 2, 3, 4, 5, 6, 7, 8, 9, 10, 11, 12, or more months or years). In such embodiments, compositions may be taken on a regular scheduled basis (e.g., daily, weekly, etc.) for the duration of the extended period.

Exemplary Procedures for Preparation of a Tomato Extract

Exemplary Procedure 1

A tomato extract for use according to the technology described is prepared, for example, using a commercially available cold-break tomato paste of 28-30° Brix (e.g., 28-30% solids (w/w)) and having a browning index of less than 0.350 AU (where the browning index is defined as the absorbance at 420 nm of a solution having 12.5 g soluble solids per liter) as the starting material. The paste is diluted, e.g., approximately 1 to 5, with ultrapure water and large particulate matter is removed by centrifugal filtration followed by clarification using a Westfalia MSB-14 Separator (a centrifugal disc clarifier) at room temperature. Smaller particulate matter is then removed by microfiltration at a temperature not exceeding 45° C. to give a clear straw-colored solution containing no insoluble (capable of being spun-down) solids and capable of passing through a 0.2 µM filter without loss of soluble solids. This solution is concentrated by evaporation to form a syrup of 62-65° Brix using carefully controlled conditions and a temperature not exceeding 80° C. to inhibit non-enzymic browning reactions. A flash pasteurization step (e.g., at 105° C. for 3 seconds) is incorporated at the outset of the evaporation procedure. The final product is typically characterized by a browning index of less than 0.600 AU and a microbial total plate count of less than 1000. The concentrated extract is added in some embodiments to an orange juice matrix for administration, e.g., to patients.

Exemplary Procedure 2

An alternative preparation of tomato extract and subfractions thereof is prepared from tomatoes to produce an aqueous extract. According to this exemplary procedure, an aqueous extract from ripe tomato fruit is prepared by homogenization of fresh tomatoes (*Lycopersicon esculentum*, sourced locally), centrifugation, and clarification of the resulting straw-colored liquid by ultrafiltration (ultrafiltration membrane, MW cut-off 1000 Da, Millipore (UK) Ltd., Watford, UK). A typical analysis demonstrates that the tomato aqueous extract consists largely of soluble sugars (85-90% of dry matter). These constituents are removed using solid phase extraction with styrene divinylbenzene (SDVB) cartridges (J T Baker, Mallinckrodt Baker B V, Deventer, Holland) at pH 2.5. Non-sugar components are retained on the cartridges and eluted in methanol. Typically, non-sugar material accounts for approximately 4% of the aqueous extract dry matter. In some embodiments, semi-preparative HPLC is used to subfractionate components from the non-sugar material into three broad groups. For example, HPLC using Synergy Polar-RP, 4 µm, 250×10 mm and Luna C18(2), 3 µm, 250×10 mm columns (Phenomenex, Macclesfield, UK) and acetonitrile/0.05% TFA gradients provides one method for this step. HPLC fractions, in some embodiments, are reconstituted to known concentrations in phosphate-buffered saline (PBS, Sigma-Aldrich, Poole, UK) and optionally adjusted to pH 7.4 before use, e.g., for in vitro experiments.

Examples

Preparation of Tomato Extract

During the development of embodiments of the technology described herein, tomato extracts were prepared and tested. In some embodiments, the tomatoes were homogenised with a Brown Turbo Mixer for 20-30 seconds at highest speed. The homogenate was then centrifuged at 9000×g for 15 minutes at 4° C. The supernatant was then boiled for 30 minutes and centrifuged again. The supernatant was removed and freeze-dried overnight. The dried material was dissolved in double distilled water and the pH was adjusted to 7.4. The samples were subjected to ultrafiltration using a Microsep™ Centrifugal Device (Pall Corporation, US) having a molecular weight cut-off of 1000 kDa. The ultrafiltrate was collected, freeze dried, and reconstituted in water; the pH was adjusted to 7.4 for further studies.

Removal of Water-Soluble Sugars from the Extract

In some embodiments of the tomato extract compositions, a tomato extract contained more than 50% inactive water soluble sugars. Accordingly, these sugars were removed from the extract. Solid phase extraction column chromatography was used for removing sugars, e.g., using a Bond Elut ENV cartridge (Agilent). The Bond Elut ENV cartridges were conditioned with 2×4 ml 100% methanol and then equilibrated with 2×4 ml distilled water. A volume of 4 ml of the prepared sample (comprising approximately 1 g of the tomato extract) was loaded onto the cartridge. Cartridges were washed with 2×3 ml of double distilled water, and then the water-soluble component was eluted from the cartridge using water. The cartridges were then dried completely before eluting the non-sugar components. After drying, the non-sugar components were eluted with 3×2 ml of 100% methanol using a slow (e.g., drop wise) flow rate and eluates were collected into tubes. The eluted samples were evaporated to dryness under $N_2$ at 45° C. and then dissolved in 500 µl of milliQ water. Both the water eluate and methanol eluate were then tested for their inhibitory activities against ACE. The freeze-dried material from each of these steps was used to test for the presence of anti-platelet activities.

Angiotensin Converting Enzyme (ACE) Assay

Angiotensin I-converting enzyme (ACE, EC 3.4.15.1) is a circulating enzyme that participates in the body's renin-angiotensin system that regulates blood pressure. During the development of embodiments of the technology provided herein, experiments were performed to test the effect of tomato extract on serum ACE activity. ACE activity was measured using the Angiotensin Converting Enzyme Assay kit.

Isolation of Anti-Hypertensive Components from Tomatoes

During the development of embodiments of the technology provided herein, tomato extracts were characterized and tested for activity against ACE. These results are summarized in Tables 1, 2, and 3 which compile data related to the isolation of embodiments of the sugar free tomato extract provided herein and the inhibitory effect of both tomato juice and sugar free tomato extract in a dose dependent manner. After preparation and testing, it was discovered that the active components of the extract are water-soluble, heat stable, and have a molecular mass less than 1000 Da. In addition, the dried material contained a high amount of soluble sugars (approximately 50%). The inactive sugars were removed by solid phase chromatography, e.g., by solid phase extraction column chromatography using a Bond Elut ENV cartridge. The yield of the sugar-free anti-hypertensive factors was 67.86 mg per 100 g of tomatoes.

TABLE 1

Preparation of tomato extract

| | |
|---|---|
| Starting weight of tomatoes | 207.89 g |
| Dry weight of boiled extract supernatant | 6.14 g |
| Dry weight after sugars removed by solid phase column chromatography | 151 mg |
| Total amount of sugar-free active materials per 100 g of tomatoes | 72.63 mg |

TABLE 2

Inhibition of human serum ACE activity by fresh tomato juice
(Juice was prepared after centrifugation at 9000×g at 4 C.
for 15 min of tomato juice

| | Volume of juice | Inhibition of ACE activity (%) |
|---|---|---|
| Tomato juice | 0 | 0 |
| Tomato juice | 10 µL | 30 |
| Tomato juice | 20 µL | 35 |
| Tomato juice | 30 µL | 40 |

TABLE 3

Inhibition of human serum ACE activity by the sugar
free tomato extract in a dose dependent manner

| | Final Concentration | Inhibition of ACE activity (%) |
|---|---|---|
| Sugar free tomato extract | 0 | 0 |
| | 0.48 mg/ml serum | 18 |
| | 0.95 mg/ml serum | 30 |
| | 1.90 mg/ml serum | 48 |
| | 2.86 mg/ml serum | 60 |
| | 3.80 mg/ml serum | 70 |
| | 5.72 mg/ml serum | 85 |

Angiotensin I-converting enzyme (ACE, EC 3.4.15.1) is a circulating enzyme that participates in the body's renin-angiotensin system regulates blood pressure. The effect of tomato juice and sugar-free tomato extract on the serum ACE activity was measured using the Angiotensin Converting Enzyme Assay REA Direct kit (radio enzymatic assay) (Buhlmann, Germany). Typically, the serum (50 µL) was incubated with different amounts of sugar free extract or volumes of kiwifruit juice for 15 min at 37 C. After the incubation the ACE activity of the serum was measured using the ACE kit.

TABLE 4

Platelet aggregation inhibitory activity of sugar-free tomato extract

| | Amount added in 0.225 ml of PRP | Inhibition of platelet aggregation (%) |
|---|---|---|
| Sugar free tomato extract | 0 | 0 |
| | 20 µL | 30 |
| | 80 µL | 60 |
| | 200 µL | 90 |

Anti-platelet activity of the sugar-free tomato extract was measured in platelet rich plasma (PRP). The pH of all samples was adjusted to 7.4 prior testing their effect on platelet aggregation. Venous blood was collected from volunteers who had not taken any medications for at least 14 days before donation. Blood (20-30 ml) was collected using a 19G butterfly needle and coagulation was prevented by mixing the blood samples with acid citrate, (135 mM) in the ratio of 9 parts by volume of blood up to 1 part by volume of acid citrate. PRP was prepared from the samples by centrifuging the blood at 180×g for 15 min. at room temperature. The amounts of tomato extract as indicated in the table was incubated with 0.225 ml of PRP at 37° C. for 15 min. after which the effect of the tomato extract on ADP induced platelet aggregation was monitored with the addition of ADP to a final concentration 3 µM. Controls were run in parallel using phosphate buffer, pH 7.4 instead of the. Platelet aggregation in PRP was monitored using Aggram, Helena, USA at a constant stirring speed of 1000 rpm at 37 C.

FIG. 1 also provides a graph depicting the effect of sugar free tomato extract on inhibition of activity of pure ACE protein. ACE activity was measured by a radioactivity assay as described. ACE enzyme from rabbit lung (Sigma product no A6778) EC 3.4.15.1 CAS number 9015-821-1 was used. Increasing amounts of ACE protein were incubated in the absence and presence of 30 uL of sugar free tomato extract (Fruitflow) for 30 min at 37 C and the residual ACE activity was then measured. The tomato extract completely almost inhibited ACE activity compared with the untreated control ACE activity.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in pharmacology, biochemistry, medical science, or related fields are intended to be within the scope of the following claims.

I claim:

1. A method of treating hypertension, comprising administering a composition comprising a tomato extract to a subject in need thereof, the composition produced by a process comprising:
   a) homogenizing tomatoes;
   b) removing particulates by centrifugation and/or ultrafiltration; and
   c) removing soluble sugars.

2. The method of claim 1, wherein the composition is a water-soluble, sugar-free tomato extract.

3. The method of claim 1, wherein the tomato extract is made from a cold-break tomato paste.

4. The method of claim 1, wherein the composition is produced by a process comprising:
   a) diluting in water a cold-break tomato paste of 28-30° Brix and a browning index less than 0.350 AU;
   b) removing particulate matter greater than 0.2 μm to produce a solution; and
   c) concentrating the solution to form a syrup of 62-65° Brix.

5. The method of claim 1, wherein the process further comprises fractionating the non-sugar components using high-pressure liquid chromatography.

6. The method of claim 1, wherein the composition comprises a tomato extract, obtained by a method comprising:
   a) homogenizing a tomato to produce a tomato homogenate;
   b) filtering the tomato homogenate through a filter having a molecular weight cutoff of 1000 Da to produce a filtrate;
   c) collecting the filtrate to provide an extract; and
   d) removing a water-soluble sugar from the extract.

7. The method of claim 1, wherein the tomato is peeled prior to the step of homogenizing.

8. The method of claim 1, wherein the tomato extract is in the form of a concentrate or a dehydrate.

9. The method of claim 8, wherein the tomato extract is in the form of a concentrate which is at least 2-fold concentrated.

10. The method of claim 1, wherein the tomato extract has been dehydrated to give a dry extract.

11. The method of claim 10, wherein the dry extract is in the form of a solid or semisolid dosage form.

12. The method of claim 1, wherein the extract is contained within a capsule shell.

13. The method of claim 1, wherein the extract contains a substantially heat stable water soluble compound or compounds having a molecular weight of less than 1000 Da.

14. The method of claim 1, wherein the extract is in the form of an active fraction of the tomato fruit capable of passing through an ultrafiltration filter having a molecular weight cut-off of 1000 Da and containing a substantially heat stable, colorless or straw-colored, water soluble compound or compounds having a molecular weight of less than 1000 Da.

15. The method of claim 1, further comprising testing the subject for the presence of hypertension.

16. The method of claim 15, further comprising continuing to administer the composition when the subject tested positive for hypertension.

* * * * *